United States Patent [19]

Tafesh et al.

[11] Patent Number: 5,220,067

[45] Date of Patent: Jun. 15, 1993

[54] PROCESS FOR THE PREPARATION OF ARYLETHYLAMINES AND SUBSTITUTED ARYLETHYLAMINES

[75] Inventors: Ahmed Tafesh; B. Frank Wood; Joseph A. McDonough; Graham N. Mott, all of Corpus Christi, Tex.

[73] Assignee: Hoechst Celanese Corporation, Somerville, N.J.

[21] Appl. No.: 859,774

[22] Filed: Mar. 30, 1992

[51] Int. Cl.⁵ ........................................... C07C 209/40
[52] U.S. Cl. ..................................... 564/375; 562/59; 562/66; 562/125; 564/323; 564/337; 564/374; 564/378; 564/382
[58] Field of Search ............... 564/323, 337, 374, 375, 564/378, 381, 382; 562/59, 66, 125

[56] References Cited

U.S. PATENT DOCUMENTS 5,041,669  8/1991  Tafesh et al. ........................ 564/337

Primary Examiner—Richard L. Raymond
Attorney, Agent, or Firm—Donald R. Cassady; James J. Mullen; P. S. Kalyanaraman

[57] ABSTRACT

This invention provides a process for directly preparing hydrohalide salts of arylethylamines from (α-chloro-α-oximino)acetophenones. The process involves hydrogenation in presence of a transition metal catalyst in an organic acid in substantial absence of moisture. The process is illustrated by conversion of 4-hydroxy (α-chloro-α-oximino)acetophenone to Tyramine hydrochloride:

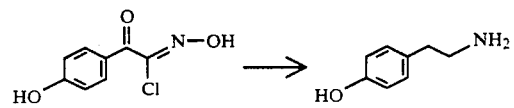

21 Claims, No Drawings

PROCESS FOR THE PREPARATION OF ARYLETHYLAMINES AND SUBSTITUTED ARYLETHYLAMINES

This invention discloses a process for preparing arylethylamines and substituted arylethylamines by hydrogenation reduction of (α-halo-α-oximino)acetophenones, and substituted (α-halo-α-oximino)acetophenones.

BACKGROUND OF THE INVENTION

Substituted and unsubstituted arylethylamines are chemical intermediates of commercial significance. They are used in the preparation of pharmacologically active compounds and, in some instances, are themselves pharmacologically active. For example, phenethylamine and p-hydroxyphenethylamine (Tyramine) have sympathomimetic (adrenergic) action. Tyramine is also a moiety in opiates, and is useful as an intermediate or substituent in the preparation of other physiologically active compounds or compositions. Tyramine hydrochloride is an important pharmaceutical intermediate used for the preparation of bezafibrate, an anticholesterol agent. Hydroxytyramine (dopamine) is a pharmacologically important neural inhibitory transmitter. It is the active ingredient in the pharmaceutical compounds, Dopastat and Intropin. It also represents the naturally occurring immediate precursor of norepinephrine.

Because of the importance of arylethylamines, accounts of their synthesis are well known. Some of them are: U.S. Pat. Nos. 1,995,709; 2,567,906; 2,505,645; 2,784,228; and 3,966,813; *Journal of Medicinal Chemistry*, vol. 25, p. 1442 (1982); *J. Chem. Society*, Vol. 95, p. 1127 (1909); *J. Amer. Chem. Society*, Vol. 55, p. 3389 (1933), and *Hakko Kooaku Kaishi*, Vol. 55(2), pp. 68–74 (1977).

U.S. Pat. No. 5,041,669 (assigned to Hoechst Celanese Corporation) describes the synthesis of arylethylamines from acetophenones. The acetophenones are first converted to α-oximino acetophenones which are then hydrogenated to arylethylamines.

Pending U.S. patent application No. 07/630,127, filed Dec. 19, 1990, now abandoned, describes the synthesis of arylethylamine hydrochlorides by hydrogenation reduction of α-oximino acetophenones in an aqueous reaction medium.

There is a continuing interest in identifying improved and cost effective methods to prepare arylethylamines, preferably from readily available materials or materials that may be produced readily and economically. For instance, synthesis of (α-halo-α-oximino)acetophenones is known. U.S. patent application, Ser. No. 07/801,999, filed Dec. 3, 1991, describes the synthesis of 4-hydroxy (α-chloro-α-oximino)acetophenone (N,4-dihydroxy-α-oxobenzene-ethanimidoyl chloride). Compounds like 4-hydroxy (α-chloro-α-oximino)acetophenone are known to yield aryl aminoethanol hydrochlorides on reduction with lithium aluminum hydride, according to H. Brachwitz, *Zeitschrift fur Chemie.* Vol. 14(7), 268 (1974).

SUMMARY OF THE INVENTION

The present invention includes a method of directly preparing arylethylamines and their hydrohalide salts from (α-halo-60 -oximino)acetophenones. The method comprises:

(a) providing an (α-halo-α-oximino)acetophenone of Formula 1:

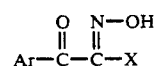

wherein X is a halide selected from F, Cl, Br, or I; and wherein Ar is an unsubstituted or substituted phenyl or naphthyl radical, wherein the substituents are selected from the group consisting of amino, alkylamino, dialkylamino, hydroxyl, alkoxy, alkyl, phenyl, benzyl, sulfonic acid, and sulfinic acid radicals, wherein the alkyl component is a branched or unbranched C1-C8 alkyl radical and wherein any of said alkyl, phenyl, and benzyl radicals are optionally substituted with one or more substituents selected from amino, hydroxyl, sulfonic acid, and sulfinic acid radicals, and said phenyl and benzyl substituents are optionally substituted with a C1-C8 alkyl or C1-C8 alkoxy radical or both;

(b) reacting the acetophenone compound in step (a) with hydrogen, in a substantially anhydrous organic acid solvent, under substantially anhydrous conditions and in the presence of a hydrogenation catalyst comprising a transition metal on an inert support, in order to consume about five equivalents of hydrogen; and (c) removing the catalyst and isolating the arylethylamine.

The reaction steps are advantageously conducted in one pot.

DESCRIPTION OF THE INVENTION

The present invention provides, in one embodiment, a process for direct conversion of (α-halo-α-oximino)acetophenones to arylethylamines, as described in Scheme I:

Scheme I

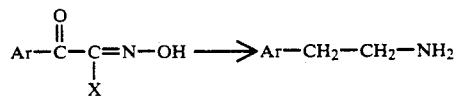

wherein X and Ar are as described above. As an illustration, when X is Cl, and Ar is 4-hydroxyphenyl, the starting compound is 4-hydroxy (α-chloro-α-oximino)acetophenone (Formula 2 infra), and the product is Tyramine hydrochloride.

The reaction of Scheme I is a catalytic hydrogenation and is conducted in an organic acid solvent in which the compound of Formula 1 is preferably dissolved. The concentration of 1 in the medium is generally in the range of about 5–30 wt %, typically about 10–20 wt %, and preferably about 12–15 wt %. The acid solvent is an organic acid such as, for example, acetic acid, propionic acid, the butyric acids, the pentanoic acids, and the like. It is essential, however, that the acid chosen is substantially anhydrous during step (b) above, and the hydrogenation conditions are substantially moisture-free. The term "substantially anhydrous" refers to limitation of water content to less than about 1% by weight in the solvent. Such anhydrous acid solvents are commercially available. Substantially moisture-free conditions are achieved generally by maintaining an inert gas atmosphere, as is well known to those skilled in the art. Maintaining an inert gas atmosphere also helps in safe operation, since some of the reaction mixtures may tend to become flammable in presence of air or oxygen. Furthermore, oxygen may deactivate the catalyst.

The hydrogenation is catalyzed by catalysts of the transition metal type on an inert support. Such catalysts are well known and available. Examples of catalytically active transition metals include Pt, Pd, Raney Ni, Rh, and combinations thereof. Palladium and platinum are preferred with palladium being the most preferred. A preferred inert support is carbon. Such catalysts are commercially available as Pd/C, Pt/C, and the like. The catalyst is generally used in a concentration of about 0.05 to about 20 weight percent based on compound of Formula 1, typically in the range of about 0.5–10 weight percent and preferably in about 2–6 weight percent. The hydrogenation is generally conducted at about 30°–120° C., typically at about 40°–100° C., and preferably at around 50°–95° C. The pressure range for hydrogenation during the hydrogenation is generally about 0–1000 psi, typically about 0–500 psi, and preferably about 0–300 psi.

As noted above, the solvent for step (b) must be substantially anhydrous. This is because ($\alpha$-halo-$\alpha$-oximino)acetophenones of Formula 1 may either undergo facile hydrolysis by water similar to acid halides, due to their structural similarity, or may ionize to an intermediate which may then dimerize or decompose. Thus, if the solvent is not substantially anhydrous, any water in the solvent may lead to undesired products, in addition to or instead of, the desired arylethylamine salt, depending upon the amount of water in the reaction. However, by employing a substantially anhydrous solvent as well as moisture-free conditions during step (b) of the reaction, the formation of any such by-products can be significantly reduced or avoided.

In a particularly preferred embodiment, the process of the present invention may be illustrated by the conversion of 4-hydroxy ($\alpha$-chloro-$\alpha$-oximino)acetophenone (Formula 2) to Tyramine (Formula 3), as shown in Scheme II:

Scheme II

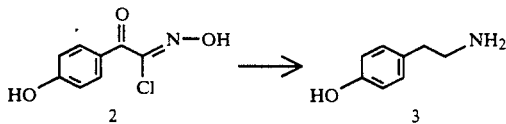

Thus, 4-hydroxy ($\alpha$-chloro-$\alpha$-oximino)acetophenone (2) is taken in a hydrogenation apparatus such as, for example, an autoclave, and a transition metal catalyst on an inert support such as, for example, 10% Pd/C is added to it. The atmosphere in the autoclave is made substantially moisture-free by providing an atmosphere of nitrogen, which gas is then replaced by hydrogen. A substantially anhydrous acid solvent such as, for example, glacial acetic acid, is then added into the autoclave, and the hydrogenation is carried out to a total consumption of about five equivalents of hydrogen, at initial temperatures of around 20° C. which is raised during the reaction to around 70° C. Removal of the catalyst produces Tyramine in yields as high as 90%.

The following Examples are provided in order to further illustrate the present invention; however, the invention is no way limited thereby.

EXAMPLES

In the following Examples, g refers to grams, ml to milliliters, ° C. to degrees Celsius, rpm to revolutions per minute, psi to pounds per square inch, and ambient temperature to temperatures about 21°–28° C.

EXAMPLE 1

Preparation of 4-hydroxy ($\alpha$-chloro-$\alpha$-oximino)acetophenone:

This compound was prepared following the procedure described in the above-referred U.S. patent application Ser. No. 07/801,999.

A nitrosyl chloride generator was set up by fitting a 1 liter, four neck flask with a mechanical stirrer, an inlet for adding nitrite solution, a gas outlet, and a thermocouple. A reaction flask was also set up by fitting a 1 liter, four neck flask with a mechanical stirrer, a gas sparger which was connected to the gas outlet from the nitrosyl chloride generator, a thermocouple, and a Dewar condenser charged with dry ice/isopropanol. The head space in the reaction flask was swept with dry nitrogen at the rate of about 0.5 standard cubic feet per hour to ensure that an explosive mixture of solvent vapor, NO, and $N_2O$ was not formed. All gases from the reaction flask exited via the Dewar condenser.

The reaction flask was charged with 4-hydroxyacetophenone (50 g, 0.37 moles), and diisopropyl ether containing about 1 M HCl (375 ml). The acetophenone was suspended in the ether. The reaction flask was cooled to about 5° C. The nitrosyl chloride generator was charged with hydrochloric acid (30.5%, 535 g, 4.5 moles). Aqueous $NaNO_2$ (40%, 190.4 g, 1.1 moles) was introduced into the generator with a peristaltic pump at a constant rate such that the total addition time was about 6 hours. NOCl formed in the generator flowed into the reaction flask via the sparger. The rate of nitrite addition together with external cooling maintained the reaction at about 5°–10° C. Toward the end of the addition, the solids in the reaction dissolved to form a greenish brown solution. After the addition was complete, the generator was sparged with nitrogen for about an hour to remove any remaining NOCl into the reaction flask. The reaction mixture was allowed to stand overnight at ambient temperature. The reaction mixture was transferred to a vacuum distillation system and the solvent was removed under vacuum (about 250 torr) to deposit 4-hydroxy ($\alpha$-chloro-$\alpha$-oximino)acetophenone (yield: 77%).

EXAMPLE 2

Preparation of Tyramine hydrochloride in acetic acid

A 300 ml autoclave was loaded with 10% Pd/C catalyst (3.2 g), and 4-hydroxy ($\alpha$-chloro-$\alpha$-oximino)acetophenone (8.8 g). It was then purged three times with nitrogen, and then three times with hydrogen. It was then pressurized to 50 psi with hydrogen to prereduce the catalyst. Glacial acetic acid (72 ml) was added into the reactor through the blow case. The reactor was again pressurized with hydrogen to 50 psi. Hydrogenation was started at around ambient temperature by internal stirring at about 1500 rpm, but after about three equivalents of hydrogen were consumed, the hydrogen consumption slowed down. The temperature was increased to about 60° C. over about an hour. The total time for consumption of five equivalents of hydrogen was about 7 hours. After the reaction, the catalyst was filtered hot, and the filtrates were cooled to yield Tyramine (90% yield).

What is claimed is:

1. A method of preparing the hydrohalide salt of an arylethylamine, which comprises:
   (a) providing a compound of the formula:

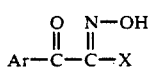

wherein X is a halide selected from F, Cl, Br, or I; and
   wherein Ar is an unsubstituted or substituted phenyl or naphthyl radical, wherein the substituents are selected from the group consisting of amino, alkylamino, dialkylamino, hydroxyl, alkoxy, alkyl, phenyl, benzyl, sulfonic acid, and sulfinic acid radicals, wherein the alkyl component is a branched or unbranched C1-C8 alkyl radical and wherein any of said alkyl, phenyl, and benzyl radicals are optionally substituted with one or more substituents selected from amino, hydroxyl, sulfonic acid, and sulfinic acid radicals, and said phenyl and benzyl substituents are optionally substituted with a C1-C8 alkyl or C1-C8 alkoxy radical or both;
   (b) reacting the compound in step (a) with hydrogen, in an organic acid solvent, under substantially anhydrous conditions and in the presence of a hydrogenation catalyst comprising a transition metal on an inert support, in order to consume about five equivalents of hydrogen; and
   (c) removing the catalyst and isolating the arylethylamine salt.

2. The method as described in claim 1, wherein said organic acid is selected from the group consisting of acetic acid, propionic acid, the butyric acids, and the pentanoic acids.

3. The method as described in claim 1, wherein said organic acid is acetic acid.

4. The method as described in claim 1, wherein said compound is present in concentrations of about 5-20 weight percent in said organic acid in step (b).

5. The method as described in claim 1, wherein said transition metal is selected from the group consisting of platinum, palladium, nickel, rhodium, ruthenium, and combinations thereof.

6. The method as described in claim 1, wherein said transition metal comprises palladium.

7. The method as described in claim 1, wherein said transition metal comprises platinum.

8. The method as described in claim 1, wherein said inert support is carbon.

9. The method as described in claim 1, wherein Ar is a phenyl substituted at the para position with a hydroxyl.

10. The method as described in claim 1, wherein X is Cl.

11. The method as described in claim 1, wherein said step (b) is conducted at a temperature of about 10°-120° C.

12. The method as described in claim 11, wherein said temperature in step (b) is about 15°-90° C.

13. The method as described in claim 11, wherein said temperature in step (b) is about 20°-80° C.

14. The method as described in claim 1, wherein said transition metal is present in about 0.05-20 weight percent.

15. The method as described in claim 1, wherein said transition metal is present in about 0.5-10 weight percent.

16. The method as described in claim 1, wherein said transition metal is present in about 2-6 weight percent.

17. The method as described in claim 1, wherein said hydrohalide salt of arylethylamine is further converted to arylethylamine by basification.

18. A method of preparing Tyramine hydrochloride from 4-hydroxy (α-chloro-α-oximino)acetophenone, which comprises:
   (a) providing a solution of said acetophenone in a substantially anhydrous organic acid solvent in about 10 weight percent concentration;
   (b) reacting said solution at temperatures of about 20°-80° C. with hydrogen in the presence of a transition metal catalyst on an inert support, in order to consume about five equivalents of hydrogen; and
   (c) removing said catalyst and isolating Tyramine hydrochloride.

19. The method as described in claim 18, wherein said organic acid is acetic acid.

20. The method as described in claim 18, wherein said transition metal catalyst comprises palladium.

21. The method as described in claim 18, wherein said catalyst is present in about 0.05-10 weight percent based on said acetophenone.

* * * * *